United States Patent
Ziemer et al.

(10) Patent No.: US 6,914,035 B2
(45) Date of Patent: Jul. 5, 2005

(54) COMBINATIONS OF HERBICIDES AND SAFENERS

(75) Inventors: Frank Ziemer, Kriftel (DE); Lothar Willms, Hofheim (DE); Christopher Rosinger, Hofheim (DE); Hermann Bieringer, Eppstein (DE); Erwin Hacker, Hochheim (DE)

(73) Assignee: Bayer CropScience GmbH, Frankfurt (DE)

( * ) Notice: Subject to any disclaimer, the term of this patent is extended or adjusted under 35 U.S.C. 154(b) by 7 days.

(21) Appl. No.: 10/241,136

(22) Filed: Sep. 11, 2002

(65) Prior Publication Data

US 2003/0130120 A1 Jul. 10, 2003

(30) Foreign Application Priority Data

Sep. 13, 2001 (DE) .......................... 101 45 019

(51) Int. Cl.⁷ .................. A01N 43/00; A01N 43/80
(52) U.S. Cl. .................. 504/144; 504/130; 504/139; 504/140; 504/141; 504/149
(58) Field of Search ................. 504/112, 130, 504/139, 140, 141, 149, 144

(56) References Cited

U.S. PATENT DOCUMENTS

| | | | |
|---|---|---|---|
| 6,063,732 A | 5/2000 | Ruegg | 504/140 |
| 6,251,827 B1 | 6/2001 | Ziemer et al. | 504/130 |
| 2001/0044382 A1 | 11/2001 | Ruegg | 504/139 |

FOREIGN PATENT DOCUMENTS

| | | |
|---|---|---|
| CA | 2335945 | 12/1999 |
| WO | WO 97/34485 | 9/1997 |
| WO | WO 99/16744 | 4/1999 |
| WO | WO 99/66795 | 12/1999 |
| WO | WO 00/00031 | 1/2000 |
| WO | WO 00/30447 | 6/2000 |
| WO | WO 01/17350 | 3/2001 |

Primary Examiner—Sabiha Qazi
(74) Attorney, Agent, or Firm—Connolly Bove Lodge & Hutz LLP

(57) ABSTRACT

Herbicidal compositions comprising at least one herbicidally active compound of the formula (I) and at least one crop-plant-protecting compound of the formula (II) as safener are described.

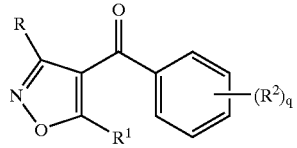

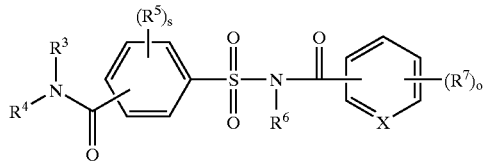

15 Claims, No Drawings

COMBINATIONS OF HERBICIDES AND SAFENERS

The invention relates to the technical field of crop protection compositions, in particular herbicide/antidote combinations (active compound/safener combinations), which are highly suitable for use against competing harmful plants in crops of useful plants.

Combinations of herbicides from the group of the inhibitors of hydroxyphenylpyruvate dioxygenase (HPPD), including, for example, benzoylcyclohexanediones, benzoylpyrazoles and benzoylisoxazoles, with safeners are known in principle. Thus, WO 00/30447 and WO 01/17350 each describe combinations of numerous herbicides from the group of the HPPD inhibitors with a large number of safeners of different structures. However, the combinations, disclosed specifically in these applications, of herbicides of the type of the benzoylisoxazoles with safeners are not always sufficiently tolerated in crops of useful plants.

It has now been found that selected combinations of herbicidally active benzoylisoxazoles with certain safeners are highly compatible in crops of useful plants and, at the same time, highly effective against unwanted harmful plants.

Accordingly, the present invention provides a herbicidally active composition, comprising a mixture of A) a herbicidally effective amount of one or more compounds of the formula (I)

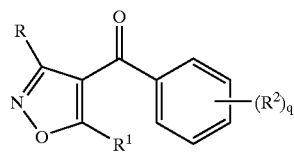

where the symbols and indices are as defined below:

R is hydrogen or $(C_1-C_4)$-alkoxycarbonyl;
$R^1$ is hydrogen, $(C_1-C_4)$-alkyl, $(C_2-C_4)$-alkenyl, $(C_2-C_4)$-alkynyl, $(C_3-C_8)$-cycloalkyl, $(C_3-C_8)$-cycloalkenyl, $(C_1-C_4)$-alkyl-$(C_3-C_8)$-cycloalkyl, $(C_3-C_7)$-halocycloalkyl, $(C_1-C_4)$-alkylthio-$(C_3-C_8)$-cycloalkyl, $(C_1-C_8)$-haloalkyl or $(C_2-C_8)$-haloalkenyl, preferably $(C_3-C_7)$-cycloalkyl, $(C_1-C_4)$-alkyl-$(C_3-C_7)$-cycloalkyl;
$R^2$ are identical or different radicals from the group consisting of halogen, nitro, cyano, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_2-C_4)$-haloalkynyl, $(C_1-C_4)$-alkoxy-$(C_1-C_4)$-alkyl, $(C_1-C_4)$-alkylthio, $(C_1-C_4)$-alkylsulfinyl, $(C_1-C_4)$-alkylsulfonyl, $(C_1-C_4)$-alkoxy-$(C_1-C_4)$-alkoxy, $(C_1-C_4)$-alkylcarbonyl, $(C_1-C_4)$-alkylsulfonylamino, $(C_1-C_4)$-alkoxy, $(C_1-C_4)$-alkoxycarbonyl, $(C_1-C_4)$-alkylaminosulfonyl, $(C_1-C_4)$-dialkylaminosulfonyl, $(C_1-C_4)$-dialkylcarbamoyl, $(C_1-C_4)$-haloalkylthio, $(C_1-C_4)$-alkylsulfonyloxy and $(C_1-C_4)$-haloalkoxy;
q is 0, 1, 2, 3 or 4; and B) an antidotically effective amount of one or more safeners from the group of the acylsulfamoylbenzamides of the formula (II), if appropriate also in the form of a salt,

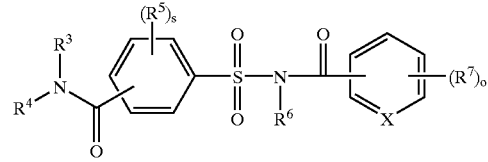

in which

X is CH or N;
$R^3$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl having up to three heteroatoms from the group consisting of nitrogen, oxygen and sulfur, where the seven last mentioned radicals are unsubstituted or substituted by one or more identical or different substituents from the group consisting of halogen, $(C_1-C_6)$-alkoxy, $(C_1-C_6)$-haloalkoxy, $(C_1-C_2)$-alkylsulfinyl, $(C_1-C_2)$-alkylsulfonyl, $(C_3-C_6)$-cycloalkyl, $(C_1-C_4)$-alkoxycarbonyl, $(C_1-C_4)$-alkylcarbonyl and phenyl and, in the case of cyclic radicals, also $(C_1-C_4)$-alkyl and $(C_1-C_4)$-haloalkyl;
$R^4$ is hydrogen, $(C_1-C_6)$-alkyl, $(C_2-C_6)$-alkenyl, $(C_2-C_6)$-alkynyl, where the three last mentioned radicals are unsubstituted or substituted by one or more identical or different substituents from the group consisting of halogen, hydroxyl, $(C_1-C_4)$-alkyl, $(C_1-C_4)$-alkoxy and $(C_1-C_4)$-alkylthio, or
$R^3$ and $R^4$ together with the nitrogen atom that carries them form a pyrrolidinyl or piperidinyl radical;
$R^5$ are identical or different radicals from the group consisting of halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulfonyl, $(C_1-C_4)$-alkoxycarbonyl and $(C_1-C_4)$-alkylcarbonyl;
$R^6$ is hydrogen, $(C_1-C_4)$-alkyl, $(C_2-C_4)$-alkenyl or $(C_2-C_4)$-alkynyl;
$R^7$ are identical or different radicals from the group consisting of halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulfinyl, $(C_1-C_4)$-alkylsulfonyl, $(C_1-C_4)$-alkoxycarbonyl or $(C_1-C_4)$-alkylcarbonyl;
s is 0, 1 or 2 and
o is 1 or 2, including the stereoisomers and the salts customarily used in agriculture.

In the context of the invention, herbicidally effective amount is to be understood as meaning an amount of one or more herbicides, which amount is suitable to effect plant growth negatively.

In the context of the invention, antidotically effective amount is to be understood as meaning an amount of one or more safeners suitable to counteract the phytotoxic action of a herbicide or herbicide mixture in a useful plant at least in part.

Unless specifically defined otherwise, the following definitions apply to the radicals in the formulae (I) and (II) and in general.

The radicals alkyl, alkoxy, haloalkyl, haloalkoxy, alkylamino and alkylthio, and the corresponding unsaturated and/or substituted radicals, can in each case be straight-chain or branched in the carbon skeleton. Alkyl radicals, also in composed meanings, such as in alkoxy, haloalkyl, etc., preferably have 1 to 4 carbon atoms and are, for example, methyl, ethyl, n- or isopropyl, n-, iso-, t- or 2-butyl. Alkenyl and alkynyl radicals have the meanings of the possible unsaturated radicals which correspond to the alkyl radicals; alkenyl is, for example, allyl, 1-methylprop-2-en-1-yl, 2-methyl-prop-2-en-1-yl, but-2-en-1-yl, but-3-en-1-yl, 1-methyl-but-3-en-1-yl and 1-methyl-but-2-en-1-yl. Alkynyl is, for example, propargyl, but-2-yn-1-yl, but-3-yn-1-yl, 1-methylbut-3-yn-1-yl. "$(C_1-C_4)$-Alkyl" is the short notation for alkyl having 1 to 4 carbon atoms; this applies correspondingly to other general definitions of radicals where the possible number of carbon atoms is given in brackets.

Cycloalkyl is preferably a cyclic alkyl radical having 3 to 8, preferably 3 to 7, particularly preferably 3 to 6, carbon atoms, for example cyclopropyl, cyclobutyl, cyclopentyl and cyclohexyl. Cycloalkenyl and cycloalkynyl are the corresponding unsaturated compounds.

Halogen is fluorine, chlorine, bromine or iodine. Haloalkyl, haloalkenyl and halo-alkynyl are alkyl, alkenyl and alkynyl, respectively, which are partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$. Haloalkoxy is, for example, $OCF_3$, $OCHF_2$, $OCH_2F$, $CF_3CF_2O$, $OCH_2CF_3$ and $OCH_2CH_2Cl$. This applies correspondingly to other halogen-substituted radicals.

Heterocyclic ring, heterocyclic radical or heterocyclyl is a mono-, bi- or polycyclic ring system which is saturated, unsaturated and/or aromatic and contains one or more, preferably 1 to 4, heteroatoms, preferably from the group consisting of N, S and O.

Preference is given to saturated heterocycles having 3 to 7 ring atoms and one or two heteroatoms from the group consisting of N, O and S, where the chalcogens are not adjacent. Particular preference is given to monocyclic rings having 3 to 7 ring atoms and one heteroatom from the group consisting of N, O and S, and also to morpholine, dioxolane, piperazine, imidazoline and oxazolidine. Very particularly preferred saturated heterocycles are oxirane, pyrrolidone, morpholine and tetrahydrofuran.

Preference is also given to partially unsaturated heterocycles having 5 to 7 ring atoms and one or two heteroatoms from the group consisting of N, O and S. Particular preference is given to partially unsaturated heterocycles having 5 or 6 ring atoms and one heteroatom from the group consisting of N, O and S. Very particularly preferred partially unsaturated heterocycles are pyrazoline, imidazoline and isoxazoline.

Preference is also given to heteroaryl, for example to mono- or bicyclic aromatic heterocycles having 5 or 6 ring atoms including one to four heteroatoms from the group consisting of N, O, S, where the chalcogenes are not adjacent. Particular preference is given to monocyclic aromatic heterocycles having 5 or 6 ring atoms including one heteroatom from the group consisting of N, O and S, and also to pyrimidine, pyrazine, pyridazine, oxazole, thiazole, thiadiazole, oxadiazole, pyrazole, triazole and isoxazole. Very particular preference is given to pyrazole, thiazole, triazole and furan.

Substituted radicals, such as substituted alkyl, alkenyl, alkynyl, phenyl or substituted heterocyclyl, denote a substituted radical derived from the unsubstituted parent radical, where the substituents are one or more, preferably 1, 2 or 3, in the case of Cl and F also up to the maximum possible number, of substituents from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl and, in the case of cyclic radicals, also alkyl and haloalkyl, and unsaturated aliphatic substituents which correspond to the saturated hydrocarbon-containing substituents mentioned, preferably alkenyl, alkynyl, alkenyloxy, alkynyloxy. Among radicals having carbon atoms, preference is given to those having 1 to 4 carbon atoms, in particular 1 or 2 carbon atoms. Preference is given to substituents from the group consisting of halogen, for example fluorine or chlorine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano. Particular preference is given here to the substituents methyl, methoxy and chlorine.

Mono- or disubstituted amino is a chemically stable radical from the group of the substituted amino radicals which are N-substituted, for example, by one or two identical or different radicals from the group consisting of alkyl, alkoxy, acyl and aryl; preferably monoalkylamino, dialkylamino, acylamino, arylamino, N-alkyl-N-arylamino and N-heterocycles. Preference is given to alkyl radicals having 1 to 4 carbon atoms. Aryl is preferably phenyl. Substituted aryl is preferably substituted phenyl. For acyl, the definition mentioned further below applies, preferably $(C_1-C_4)$-alkanoyl. This applies correspondingly to substituted hydroxylamino or hydrazino.

Unsubstituted or substituted phenyl is preferably phenyl which is unsubstituted or mono- or polysubstituted, preferably up to three times, in the case of halogen such as Cl and F also up to five times, by identical or different radicals from the group consisting of halogen, $(C_1-C_4)$-alkyl, $(C_1-C_4)$-alkoxy, $(C_1-C_4)$-haloalkyl, $(C_1-C_4)$-haloalkoxy and nitro, for example o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

An acyl radical is the radical of an organic acid having preferably up to 6 carbon atoms, for example the radical of a carboxylic acid and radicals of acids derived therefrom, such as thiocarboxylic acid, unsubstituted or N-substituted iminocarboxylic acids, or the radical of carbonic monoesters, unsubstituted or N-substituted carbaminic acids, sulfonic acids, sulfinic acids, phosphonic acids, phosphinic acids. Acyl is, for example, formyl, alkylcarbonyl, such as $(C_1-C_4$-alkyl)carbonyl, phenylcarbonyl, where the phenyl ring may be substituted, for example as mentioned above for phenyl, or alkyloxycarbonyl, phenyloxycarbonyl, benzyloxycarbonyl, alkylsulfonyl, alkylsulfinyl or N-alkyl-1-iminoalkyl.

The formulae (I) and (II) also embrace all stereoisomers in which the attachment to the atoms is topologically the same, and mixtures thereof. Such compounds contain one or more asymmetric carbon atoms or else double bonds which are not specifically shown in the general formulae. The possible stereoisomers defined by their specific spatial form, such as enantiomers, diastereomers, Z and E isomers, can be obtained by customary methods from mixtures of the stereoisomers, or else be prepared by stereoselective reactions in combination with the use of stereochemically pure starting materials.

According to the invention, suitable herbicidally active compounds are those compounds of the formula (I) which cannot be used on their own, or not optimally, in monocotyledonous crop plants such as, for example, crops of cereals, rice, millet, sugar cane and/or corn because they cause too much damage to the crop plants.

Herbicides of the formula (I) are known, for example, from EP-A 0 137 963, EP-A 0 352 543, EP-A 0 418 175, EP-A 0 496 631 and AU-A 672 058. The compounds of the formula (II) are known, for example, from WO 99/19744. The publications cited contain detailed information on preparation processes and starting materials. These publications are expressly, by way of reference, incorporated into this description.

Of particular significance are herbicide/safener combinations comprising herbicides of the formula (I) in which the symbols are as defined below:

R is hydrogen or ethoxycarbonyl;
$R^1$ is cyclopropyl and
$R^2$ are identical or different radicals from the group consisting of halogen, methyl, ethyl, trifluoromethyl, methylthio, ethylthio, methylsulfonyl, ethylsulfonyl, methoxy, ethoxy, halomethoxy and haloethoxy.

Preference is given to herbicide/safener combinations comprising herbicides of the formula (I) in which the symbols and indices are as defined below:

$R^2$ are identical or different radicals from the group consisting of chlorine, bromine, fluorine, methyl, ethyl, trifluoromethyl, methylsulfonyl, ethylsulfonyl, methoxy and ethoxy;
q is 2 or 3.

Preference is also given to herbicide/safener combinations comprising herbicides of the formula (I) in which one $R^2$ is a 2-methylsulfonyl radical and a further $R^2$ is a 4-trifluoromethyl, 4-chloro or 4-bromo radical.

Particularly preference is given to herbicide/safener combinations comprising safeners of the formula (II) in which the symbols and indices are as defined below:

X is CH;
$R^3$ is hydrogen, $(C_1-C_6)$-alkyl, $(C_3-C_6)$-cycloalkyl, $(C_2-C_6)$-alkenyl, $(C_5-C_6)$-cycloalkenyl or phenyl;
$R^6$ is hydrogen;
$R^7$ are identical or different radicals from the group consisting of halogen, nitro, $(C_1-C_4)$-alkyl, $(C_1-C_4)$-haloalkyl, $(C_1-C_4)$-haloalkoxy, $(C_3-C_6)$-cycloalkyl, $(C_1-C_4)$-alkoxy, cyano, $(C_1-C_4)$-alkylthio, $(C_1-C_4)$-alkylsulfinyl, $(C_1-C_4)$-alkylsulfonyl, $(C_1-C_4)$-alkoxycarbonyl and $(C_1-C_4)$-alkylcarbonyl.

Particular preference is also given to herbicide/safener combinations comprising safeners of the formula (II) in which the symbols and indices are as defined below:

$R^3$ is $(C_2-C_6)$-alkynyl or
$R^3$ and $R^4$ together with the nitrogen atom that carries them form a pyrrolidinyl or piperidinyl radical and
$R^6$ is methyl.

Very particular preference is given to herbicide/safener combinations comprising safeners of the formula (II) in which the group "$R^3R^4N$—CO—" is located in the 4-position on the phenyl ring.

Preferred groups of herbicides of the formula (I) are listed in Tables 1 to 4 below. The following abbreviations are used:
Et=ethyl Me=methyl

TABLE 1

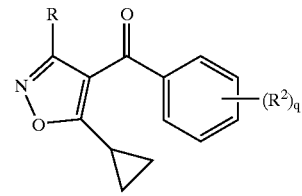

(I)

| Example No. | R | $(R^2)_q$ |
|---|---|---|
| 1-1 | H | 2-SO$_2$Me-4-CF$_3$ |
| 1-2 | H | 2-SO$_2$Me-4-Cl |
| 1-3 | H | 2-SO$_2$Me-4-Br |
| 1-4 | H | 2-SO$_2$Me-4-OCF$_3$ |
| 1-5 | H | 2,4-Cl$_2$-3-Me |
| 1-6 | H | 2-CF$_3$-4-SO$_2$Me |
| 1-7 | H | 2-Cl-4-SO$_2$Me |
| 1-8 | H | 2-Cl-4-SO$_2$Me |
| 1-9 | H | 2-SO$_2$Me-4-CF$_3$ |
| 1-10 | H | 2-Cl-3-OEt-4-SO$_2$Et |
| 1-11 | H | 2-SMe-4-CF$_3$ |
| 1-12 | H | 2-SMe-4-Br |
| 1-13 | H | 3,4-Cl$_2$-2-SMe |
| 1-14 | H | 2-SO$_2$Me-4-Cl |
| 1-15 | H | 2-NO$_2$-4-SO$_2$Me |
| 1-16 | H | 2,4-Cl$_2$-3-Me |
| 1-17 | H | 2,4-Br$_2$-3-OCH$_2$SMe |
| 1-18 | COOEt | 2,4-Br$_2$ |
| 1-19 | COOEt | 2-SO$_2$Me-4-CF$_3$ |
| 1-20 | COOEt | 2-SO$_2$Me-4-Cl |
| 1-21 | COOEt | 2-Cl-3-CO$_2$Me-4-SO$_2$Me |

The safeners (antidotes) of the formula (II) reduce or prevent phytotoxic effects which may occur when using the herbicidally active compounds of the formula (I) in crops of useful plants without substantially affecting the activity of these herbicidally active compounds against harmful plants. This allows the field of application of conventional crop protection products to be widened quite considerably and to be extended to, for example, crops such as wheat, barley, corn, rice and other crops in which use of the herbicides was hitherto impossible, or of only limited possibility, that is to say at low rates and with a restricted spectrum.

The herbicidally active compounds and the abovementioned safeners can be applied together (as a readymix or by the tank mix method) or in succession in any desired sequence. The weight ratio of safener to herbicidally active compound may vary within wide limits and is preferably within the range from 1:100 to 100:1, in particular from 1:10 to 10:1. The optimum amounts of herbicidally active substance and safener in each case depend on the type of the herbicidally active substance used or on the safener used and on the species of the plant stand to be treated and can be determined in each individual case by simple, routine preliminary experiments.

Main fields of application for the combinations according to the invention are, in particular, monocotyledonous crop plants, such as, for example, corn and cereal crops (for example wheat, rye, barley, oats), rice, sorghum, sugar cane, but also cotton and soybeans, preferably cereals, rice, millet, sugar cane and corn.

Depending on their properties, the safeners employed in accordance with the invention can be used for pretreating the seeds of a crop plant (seed dressing), or be incorporated into the seed furrows prior to sowing or applied together with the herbicide before or after plant emergence. The preemergence treatment includes both the treatment of the area under cultivation prior to sowing and the treatment of the areas under cultivation where the seeds have been planted but the plants have not yet emerged. Joint application with the herbicide is preferred. To this end, tank mixes or readymixes can be employed.

The application rates of safener required may vary within wide limits depending on the indication and the herbicidally active substance used and are generally in the range of from 0.001 to 5 kg, preferably 0.005 to 0.5 kg, of active substance per hectare.

The present invention therefore also provides a method of protecting crop plants from phytotoxic side effects of herbicides of the formula (I), which comprises applying an antidote-active amount of a compound of the formula (II) to the plants, the seeds of the plants or the area under cultivation, before, after or simultaneously with the herbicidally active substance A of the formula (I).

The herbicide/safener combination according to the invention may also be employed for controlling weed plants in crops of genetically engineered plants which are either known or still to be developed. As a rule, the transgenic plants are distinguished by particular, advantageous properties, for example by resistances to certain crop protection agents, resistances to plant diseases or pathogens causing plant diseases such as particular insects or microorganisms such as fungi, bacteria or viruses. Other particular properties relate, for example, to the harvested material in terms of quantity, quality, storing properties, composition and specific constituents. Thus, transgenic plants are known which have an increased starch content or an altered starch quality, or those where the harvested material has a different fatty acid composition.

The use of the combinations according to the invention is preferred in economically important transgenic crops of useful plants and ornamentals, for example cereals such as wheat, barley, rye, oats, millet, rice, cassava and corn or else crops of sugar beet, cotton, soya, oilseed rape, potatoes, tomatoes, peas and other types of vegetables.

When the combinations according to the invention are employed in transgenic crops, effects on weed plants to be observed in other crops are frequently accompanied by effects which are specific for application in the transgenic crop in question, for example an altered or specifically widened weed spectrum which can be controlled, altered application rates which may be used, preferably good compatibility with the herbicides to which the transgenic crop is resistant, and altered growth and yield of the transgenic crop plants.

The invention therefore also provides for the use of the combination according to the invention for controlling weed plants in transgenic crop plants.

The safeners of the formulae (II) and their combinations with one or more of the abovementioned herbicidally active substances of the formula (I) can be formulated in various ways, depending on the biological and/or chemico-physical parameters specified. Examples of suitable formulations which are possible are: wettable powders (WP), emulsifiable concentrates (EC), water-soluble powders (SP), water-soluble concentrates (SL), concentrated emulsions (BW) such as oil-in-water and water-in-oil emulsions, sprayable solutions or emulsions, capsule suspensions (CS), oil- or water-based dispersions (SC), suspoemulsions, suspension concentrates, dusts (DP), oil-miscible solutions (OL), seed dressing products, granules (GR) in the form of microgranules, spray granules, coated granules and adsorption granules, granules for soil application or broadcasting, water-soluble granules (SG), water-dispersible granules (WG), ULV formulations, microcapsules and waxes.

These individual formulation types are known in principle and described, for example, in: Winnacker-Kuchler, "Chemische Technologie" [Chemical Engineering], Volume 7, C. Hauser Verlag Munich, $4^{th}$ Edition 1986; Wade van Valkenburg, "Pesticide Formulations", Marcel Dekker N.Y., 1973; K. Martens, "Spray Drying Handbook", $3^{rd}$ Ed. 1979, G. Goodwin Ltd. London.

The formulation auxiliaries which may be required, such as inert materials, surfactants, solvents and other additives are also known and described, for example, in: Watkins, "Handbook of Insecticide Dust Diluents and Carriers", $2^{nd}$ Ed., Darland Books, Caldwell N.J., H. v. Olphen, "Introduction to Clay Colloid Chemistry", $2^{nd}$ Ed., J. Wiley & Sons, N.Y.; C. Marsden, "Solvents Guide", $2^{nd}$ Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzfl ächenaktive Äthylenoxidaddukte" [Surface-active Ethylene Oxide Adducts], Wiss. Verlagsgesell., Stuttgart 1976; Winnacker-Küchler, "Chemische Technologie" [Chemical Engineering], Volume 7, C. Hauser Verlag Munich, $4^{th}$ Edition 1986.

Based on these formulations, it is also possible to prepare combinations with other substances which act as crop protection agents, such as insecticides, acaricides, herbicides, fungicides, and also with safeners, fertilizers and/or growth regulators, for example in the form of a readymix or as a tank mix.

Wettable powders are preparations which are uniformly dispersible in water and which, besides the active substance, also comprise ionic and/or nonionic surfactants (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate, or else sodium oleoylmethyltaurinate, in addition to a diluent or inert substance. To prepare the wettable powders, the herbicidally active substances are ground finely, for example in customary apparatus such as hammer mills, blower mills and air-jet mills, and they are simultaneously or subsequently mixed with the formulation auxiliaries.

Emulsifiable concentrates are prepared, for example, by dissolving the active substance in an organic solvent such as butanol, cyclohexanone, DMF, xylene, or else higher-boiling hydrocarbons such as saturated or unsaturated aliphatics or alicycles, aromatics or mixtures of the organic solvents with the addition of one or more ionic and/or nonionic surfactants (emulsifiers). Examples of substances which can be used as emulsifiers are: calcium ($C_6$–$C_{18}$)-alkylarylsulfonates such as calcium dodecylbenzenesulfonate, or nonionic emulsifiers such as fatty acid polyglycol esters, ($C_2$–$C_{18}$)-alkylarylpolyglycol ethers, fatty alcohol polyglycol ethers, propylene oxide/ethylene oxide condensates, alkyl polyethers, sorbitan esters, such as sorbitan fatty acid esters or polyoxyethylene sorbitan esters such as polyoxyethylene sorbitan fatty acid esters.

Dusts are generally obtained by grinding the active substance with finely divided solid substances, for example talc, natural clays such as kaolin, bentonite and pyrophyllite, or diatomaceous earth.

Suspension concentrates can be water- or oil-based. They can be prepared, for example, by wet-grinding using commercially available bead mills with or without addition of surfactants, for example those which have already been mentioned above in the case of the other formulation types.

Emulsions, for example oil-in-water emulsions (EW), can be prepared, for example, by means of stirrers, colloid mills and/or static mixers using aqueous organic solvents in the presence or absence of surfactants which have already been mentioned above, for example, in the case of the other formulation types.

Granules can be prepared either by spraying the active substance onto adsorptive, granulated inert material or by applying active substance concentrates to the surface of carriers such as sand, kaolinites or granulated inert material with the aid of binders, for example polyvinyl alcohol, sodium polyacrylate or else mineral oils. Suitable active substances can also be granulated in the manner which is conventional for the preparation of fertilizer granules, if desired as a mixture with fertilizers. As a rule, water-dispersible granules are prepared by the customary processes such as spray-drying, fluidized-bed granulation, disk granulation, mixing with high-speed mixers and extrusion without solid inert material. For the preparation of disk, fluidized-bed, extruder and spray granules see, for example, "Spray-Drying Handbook" $3^{rd}$ ed. 1979, G. Goodwin Ltd., London; J. E. Browning, "Agglomeration", Chemical and Engineering 1967, pages 147 et seq.; "Perry's Chemical Engineer's Handbook", $5^{th}$ Ed., McGraw-Hill, New York 1973, p. 8–57.

For further details on the formulation of crop protection products see, for example, G. C. Klingman, "Weed Control as a Science", John Wiley and Sons, Inc., New York, 1961, pages 81–96 and J. D. Freyer, S. A. Evans, "Weed Control Handbook", $5^{th}$ Ed., Blackwell Scientific Publications, Oxford, 1968, pages 101–103.

As a rule, the agrochemical formulations comprise 0.1 to 99% by weight, in particular 0.1 to 95% by weight, of active substances of the formula (II) or of the herbicide/antidote mixture of active substances (I) and (II) and 1 to 99.9% by weight, in particular 5 to 99.8% by weight, of a solid or liquid additive and 0 to 25% by weight, in particular 0.1 to 25% by weight, of a surfactant.

In wettable powders, the active substance concentration is, for example, approximately 10 to 90% by weight, the remainder to 100% by weight being composed of customary formulation components. In the case of emulsifiable concentrates, the active substance concentration is approximately 1 to 80% by weight. Formulations in the form of dusts comprise approximately 1 to 20% by weight of active substances, sprayable solutions approximately 0.2 to 20% by weight of active substances. In the case of granules such as water-dispersible granules, the active substance content depends partly on whether the active compound is in liquid or solid form. The active substance content of the water-dispersible granules is, as a rule, between 10 and 90% by weight.

Besides this, the abovementioned formulations of active substances comprise, if appropriate, the adhesives, wetters, dispersants, emulsifiers, penetrants, preservatives, antifreeze agents, solvents, fillers, carriers, colorants, antifoams, evaporation inhibitors and pH and viscosity regulators which are customary in each case.

Co-components which can be used for the mixtures of herbicides and safeners according to the invention in mixed formulations or in a tank mix are, for example, known active substances as they are described, for example, in Weed Research 26, 441–445 (1986), or "The Pesticide Manual", $12^{th}$ edition, The British Crop Protection Council, 2000, and in the literature cited therein. Herbicides which are known from the literature and which can be combined with the mixtures according to the invention are, for example, the following active substances (note: either the common names in accordance with the International Organization for Standardization (ISO) or the chemical names, if appropriate together with the customary code number, of the compounds are given):

acetochlor; acifluorfen; aclonifen; AKH 7088, i.e. [[[1-[5-[2-chloro-4-(trifluoromethyl)-phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazin; azafenidine (DPX-R6447), azimsulfuron (DPX-A8947); aziprotryn; barban; BAS 516 H, i.e. 5-fluoro-2-phenyl-4H-3,1-benzoxazin-4-one; benazolin; benfluralin; benfuresate; bensulfuron-methyl; bensulide; bentazone; benzofluor; benzoylprop-ethyl; benzthiazuron; bialaphos; bifenox; bispyribac-sodium (KIH-2023), bromacil; bromobutide; bromofenoxim; bromoxynil; bromuron; buminafos; busoxinone; butachlor; butamifos; butenachlor; buthidazole; butralin; butroxydim (ICI-0500), butylate; cafenstrole (CH-900); carbetamide; cafentrazone; CDAA, i.e. 2-chloro-N,N-di-2-propenylacetamide; CDEC, i.e. 2-chloroallyl diethyldithiocarbamate; chlomethoxyfen; chloramben; chloransulam-methyl (XDE-565), chlorazifop-butyl, chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinidon-ethyl, cinmethylin; cinosulfuron; clethodim; clodinafop and its ester derivatives (for example clodinafop-propargyl); clomazone; clomeprop; cloproxydim; clopyralid; cumyluron (JC 940); cyanazine; cycloate; cyclosulfamuron (AC 014); cycloxydim; cycluron; cyhalofop and its ester derivatives (for example butyl ester, DEH-112); cyperquat; cyprazine; cyprazole; 2,4-DB; dalapon; desmedipham; desmetryn; di-allate; dicamba; dichlobenil; dichlorprop; diclofop and its esters such as diclofop-methyl; diclosulam (XDE-564), diethatyl; difenoxuron; difenzoquat; diflufenican; diflufenzopyr-sodium (SAN-835H), dimefuron; dimethachlor; dimethametryn; dimethenamide (SAN-582H); dimethazone, methyl 5-(4,6-dimethylpyrimidin-2-yl-carbamoylsulfamoyl)-1-(2-pyridyl)pyrazole-4-carboxylate (NC-330); triaziflam (IDH-1105), clomazon; dimethipin; dimetrasulfuron, dinitramine; dinoseb; dinoterb; diphenamid; dipropetryn; diquat; dithiopyr; diuron; DNOC; eglinazine-ethyl; EL 177, i.e. 5-cyano-1-(1,1-dimethylethyl)-N-methyl-1H-pyrazole-4-carboxamide; endothal; epoprodan (MK-243), EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl] ethanesulfonamide; ethoxyfen and its ester (for example ethyl ester, HN-252); ethoxysulfuron (from EP 342569); etobenzanid (HW 52); 3-(4-ethoxy-6-ethyl-1,3,5-triazin-2-yl)-1-(2,3-dihydro-1,1-dioxo-2-methylbenzo[b]thiophene-7-sulfonyl)urea (EP-A 079 683); 3-(4-ethyl-6-methoxy-1,3, 5-triazin-2-yl )-1-(2,3-dihydro-1,1-dioxo-2-methylbenzo[b] thiophene-7-sulfonyl)urea (EP-A 079 683); fenoprop; fenoxan, fenoxaprop and fenoxaprop-P and their esters, for example fenoxaprop-P-ethyl and fenoxaprop-ethyl; fenoxydim; fenuron; flamprop-methyl; flazasulfuron; flufonacet (BAY-FOE-5043), fluazifop and fluazifop-P, florasulam (DE-570) and their esters, for example fluazifop-butyl and fluazifop-P-butyl; fluchloralin; flumetsulam; flumeturon;

flumiclorac and its esters (for example pentyl ester, S-23031); flumioxazin (S-482); flumipropyn; flupoxam (KNW-739); fluorodifen; fluoroglycofen-ethyl; flupropacil (UBIC-4243); sodium flupyrsulfuron-methyl (DPX-KE459), fluridone; flurochloridone; fluroxypyr; flurtamone; fluthiacet-methyl (KIH-9201), fomesafen; fosamine; furyloxyfen; glufosinate; glyphosate; halosafen; halosulfuron and its esters (for example methyl ester, NC-319); haloxyfop and its esters; haloxyfop-P (=R-haloxyfop) and its esters; hexazinone; imazamethabenz-methyl; imazamox (AC-299263), imazapyr; imazaquin and salts such as the ammonium salt; imazethamethapyr; imazethapyr; imazosulfuron; iodosulfuron (methyl4-iodo-2-[3-(4-methoxy-6-methyl-1,3,5-triazin-2-yl)ureidosulfonyl]benzoate, sodium salt, WO 92/13845); ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyldymron; metabenzuron, methyl 2-[3-(4,6-dimethoxypyrimidin-2-yl) ureidosulfonyl]-4-methanesulfonamidomethylbenzoate (WO 95/10507); methobenzuron; metobromuron; metolachlor; S-metolachlor, metosulam (XRD 511); metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; N,N-dimethyl-2-[3-(4,6-dimethoxypyrimidin-2-yl)ureidosulfonyl]-4-formylaminobenzamide (WO 95/01344); naproanilide; napropamide; naptalam; NC 310, i.e. 4-(2,4-dichlorobenzoyl)-1-methyl-5-benzyloxypyrazole; neburon; nicosulfuron; nipyraclofen; nitralin; nitrofen; nitrofluorfen; norflurazon; orbencarb; oryzalin; oxadiargyl (RP-020630); oxadiazon; oxaziclomefone (MY-100), oxyfluorfen; oxasulfuron (CGA-277476), paraquat; pebulate; pendimethalin; pentoxazone (KPP-314), perfluidone; phenisopham; phenmedipham; picloram; piperophos; piributicarb; pirifenopbutyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyraflufen-ethyl (ET-751), pyrazon; pyrazosulfuron-ethyl; pyrazoxyfen; pyribenzoxim, pyridate; pyriminobac-methyl (KIH-6127), pyrithiobac (KIH-2031); pyroxofop and its esters (for example propargyl ester); quinclorac; quinmerac; quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulfentrazon (FMC-97285, F-6285); sulfazuron; sulfometuron-methyl; sulfosate (ICI-A0224); sulfosulfuron (MON-37500), TCA; tebutam (GCP-5544); tebuthiuron; tepraloxydim (BAS-620H), terbacil; terbucarb; terbuchlor; terbumeton; terbuthylazine; terbutryn; TFH 450, i.e. N,N-diethyl-3-[(2-ethyl-6-methylphenyl) sulfonyl]-1H-1,2,4-triazole-1-carboxamide; thenylchlor (NSK-850); thiazafluron; thiazopyr (Mon-13200); thidiazimin (SN-124085); thifensulfuron-methyl; thiobencarb; thiocarbazil; tralkoxydim; tri-allate; triasulfuron; triazofenamide; tribenuron-methyl; triclopyr; tridiphane; trietazine; trifluralin; triflusulfuron and esters (for example methyl ester, DPX-66037); trimeturon; tsitodef; vernolate; WL 110547, i.e. 5-phenoxy-1-[3-(trifluoromethyl)phenyl]-1H-tetrazole; UBH-509; D-489; LS 82–556; KPP-300; KPP-421, MT-146, NC-324; KH-218; DPX-N8189; DOWCO-535; DK-8910; V-53482; PP-600; MBH-001.

For use, the formulations which are in commercially available form are, if desired, diluted in the customary manner, for example using water in the case of wettable powders, emulsifiable concentrates, dispersions and water-dispersible granules. Preparations in the form of dusts, soil granules, granules for broadcasting and sprayable solutions are usually not diluted any further with other inert substances prior to use.

The necessary application rate of the herbicides of the formula (I) varies with the external conditions such as, inter alia, temperature, humidity, and the nature of the herbicide used. It may be varied within wide limits, for example between 0.001 and 10.0 kg/ha or more of herbicide, but it is preferably between 0.005 and 5 kg/ha.

The examples which follow serve to illustrate the invention:

A. FORMULATION EXAMPLES a) A dust is obtained by mixing 10 parts by weight of a compound of the formula (II) or of an active substance mixture of a herbicidally active substance of the formula (I) and a safener of the formula (II) and 90 parts by weight of talc as inert substance and comminuting the mixture in a hammer mill.

b) A wettable powder which is readily dispersible in water is obtained by mixing 25 parts by weight of a compound of the formula (II) or of an active substance mixture of a herbicidally active substance of the formula (I) and a safener of the formula (II), 64 parts by weight of kaolin-containing quartz as inert substance, 10 parts by weight of potassium lignosulfonate and 1 part by weight of sodium oleoylmethyltaurinate as wetter and dispersant, and grinding the mixture in a pinned-disk mill.

b) A dispersion concentrate which is readily dispersible or suspensible in water is obtained by mixing 20 parts by weight of a compound of the formula (II) or of an active substance mixture of a herbicidally active substance of the formula (I) and a safener of the formula (11), 6 parts by weight of alkylphenol polyglycol ether (®Triton X 207), 3 parts by weight of isotridecanol polyglycol ether (8 EO) and 71 parts by weight of paraffinic mineral oil (boiling range, for example, approx. 255 to above 277° C.) and grinding the mixture in a ball mill to a fineness of below 5 microns.

d) An emulsifiable concentrate is obtained from 15 parts by weight of a compound of the formula (II) or of an active substance mixture of a herbicidally active substance of the formula (I) and a safener of the formula (II), 75 parts by weight of cyclohexanone as solvent and 10 parts by weight of ethoxylated nonylphenol as emulsifier.

e) Water-dispersible granules are obtained by mixing

| | |
|---|---|
| 75 parts by weight | of a compound of the formula (II) or of an active substance mixture of a herbicidally active substance of the formula (I) and a safener of the formula (II) |
| 10 " | of calcium lignosulfonate, |
| 5 " | of sodium lauryl sulfate, |
| 3 " | of polyvinyl alcohol and |
| 7 " | of kaolin, | grinding the mixture on a pinned-disk mill and granulating the powder in a fluidized bed by spraying on water as granulation liquid.

f) Water-dispersible granules are also obtained by homogenizing and precomminuting, in a colloid mill,

| | |
|---|---|
| 25 part(s) by weight | of a compound of the formula (II) or of an active substance mixture of a herbicidally active substance of the formula (I) and a safener of the formula (II) |
| 5 " | of sodium 2,2'-dinaphthylmethane-6,6'-disulfonate, |
| 2 " | of sodium oleoylmethyltaurinate, |
| 1 " | of polyvinyl alcohol, |
| 17 " | of calcium carbonate and |
| 50 " | of water, | subsequently grinding the mixture on a bead mill and atomizing and drying the resulting suspension in a spray tower by means of a single-substance nozzle.

B. BIOLOGICAL EXAMPLES

B.1 Preemergence, Greenhouse

Seeds of useful plants are placed in sandy loam in pots 9–13 cm in diameter and are covered with soil. The herbicides and safeners formulated as emulsifiable concentrates or dusts are, in the form of aqueous dispersions or suspensions or emulsions, applied to the surface of the covering soil at a water application rate of 300–800 l/ha (converted), at different concentrations. For further cultivation of the plants, the pots are then kept in a greenhouse under optimum conditions. Visual scoring of the damage to useful and harmful plants takes place 3–4 weeks after the treatment.

The test results are compiled in Table 3. The reduction of the phytotoxic action for the herbicide/safener combinations according to the invention is stated in percent, compared to the herbicide applied on its own.

B.2 Postemergence, Greenhouse

Seeds of useful plants are placed in sandy loam in pots 9–13 cm in diameter and covered with soil. At the three-leaf stage, i.e. about 3 weeks after the beginning of cultivation, the test plants are treated with the herbicides (application rate 200 g of active substance per hectare) and safener (application rate 100 g of active substance per hectare) formulated as emulsifiable concentrates or dusts, in the form of aqueous dispersions or suspensions or emulsions, by spraying onto the green parts of the plants at a water application rate of 300–800 l/ha (converted). For further cultivation of the plants, the pots are kept in a greenhouse under optimum conditions. Visual scoring of the damage to useful and harmful plants takes place 2–3 weeks after the treatment.

The test results are compiled in Table 4. The reduction of the phytotoxic action for the herbicide/safener combinations according to the invention is stated in percent, compared to the herbicide applied on its own.

B.3 Preemergence, Outdoors

Seeds of useful plants are placed in sandy loam and are covered with soil. The herbicides and safeners formulated as emulsifiable concentrates or dusts are, in the form of aqueous dispersions or suspensions or emulsions, applied onto the surface of the covering soil at a water application rate of 300–800 l/ha (converted), at different concentrations. Visual scoring of the damage to useful plants takes place 29 days after the treatment.

The test results are compiled in Table 5. The reduction of the phytotoxic action for the herbicide/safener combinations according to the invention is stated in percent, compared to the herbicide applied on its own.

B.4 Seed Dressing, Preemergence, Outdoors

Corn seeds are treated (dressed) with different amounts of a safener and then placed in sandy loam and are covered with soil. The herbicides, formulated as emulsifiable concentrates or dusts, are applied to the surface of the covering soil at a water application rate of 300–800 l/ha (converted), at different concentrations. Visual scoring of the damage to useful plants takes place 41 days (examples of Table 6) or 26 days (examples of Table 7) after the treatment.

The test results are compiled in Tables 6 and 7. The reduction of the phytotoxic action for the herbicide/safener combinations according to the invention is stated in percent, compared to the herbicide applied on its own.

The herbicides and safeners used are listed in Table 2.

TABLE 2

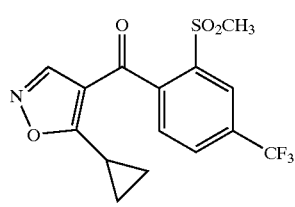

H1

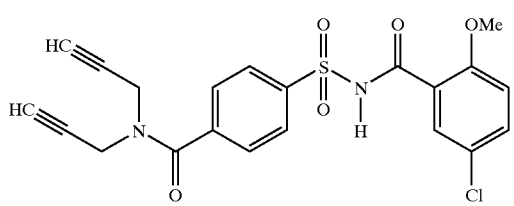

S1

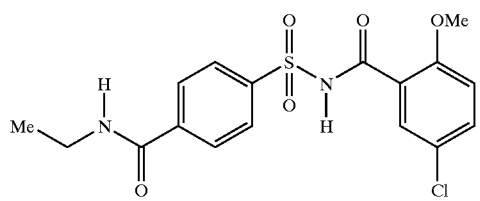

S2

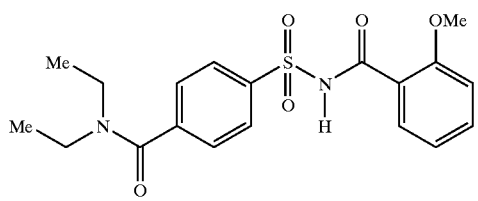

S3

TABLE 2-continued
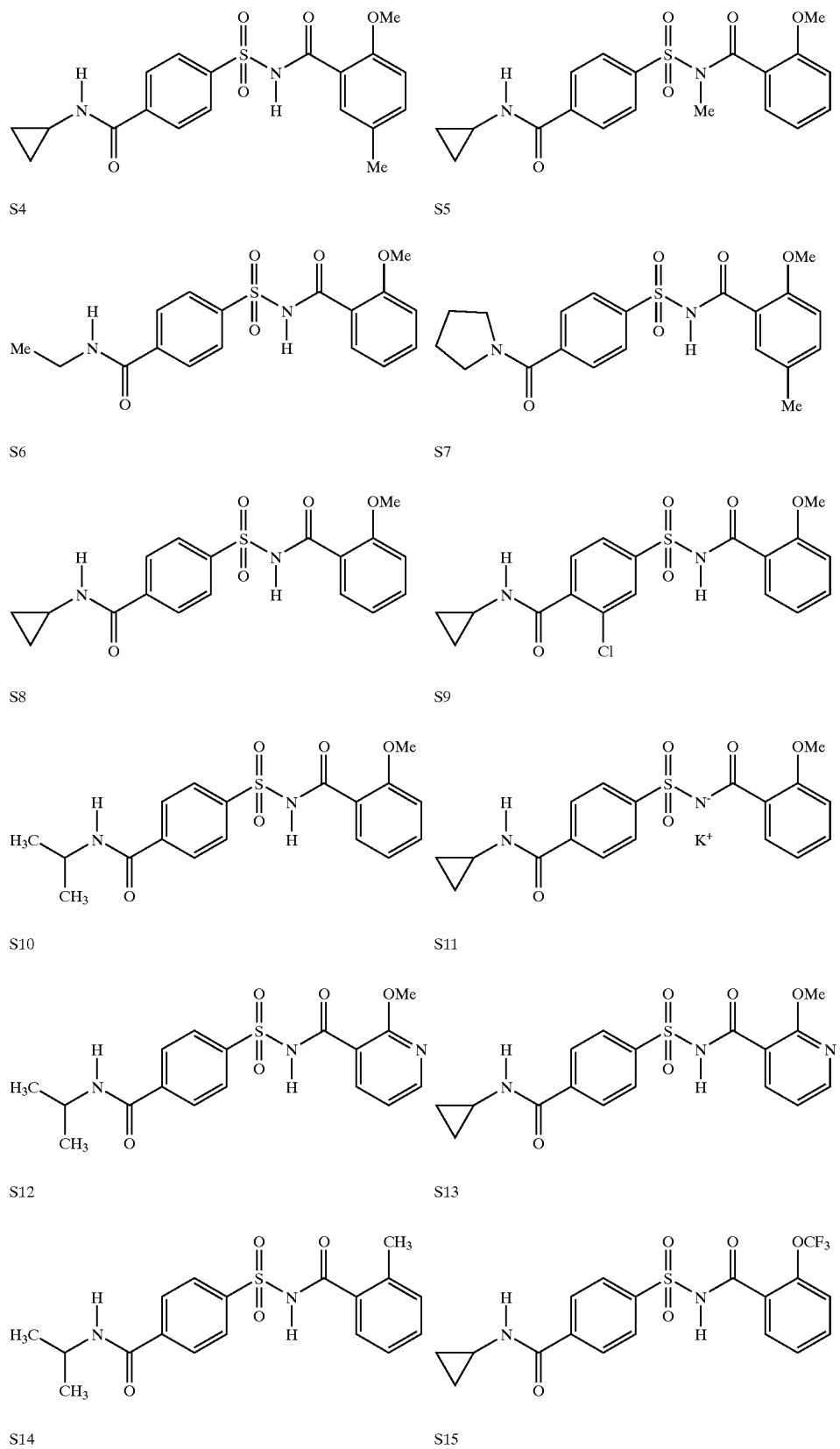

TABLE 2-continued

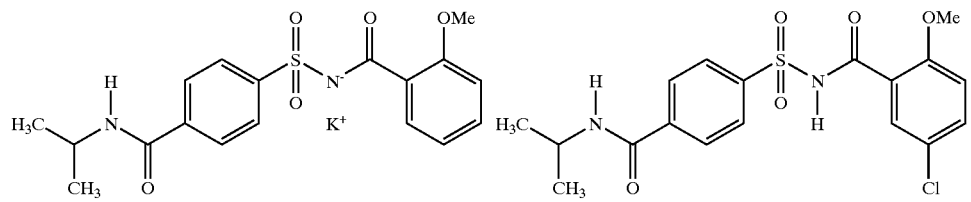

S16                                              S17

TABLE 3 preemergence, greenhouse

| No. | Herbicide + safener | Combination according to the invention Reduction of the phytotoxicity in corn by x percent |
|---|---|---|
| 3.1 | H 1 + S 1 (400 g + 200 g) | 64% (cv. DEA) |
| 3.2 | H 1 + S 2 (400 g + 200 g) | 73% (cv. DEA) |
| 3.3 | H 1 + S 3 (400 g + 200 g) | 64% (cv. DEA) |
| 3.4 | H 1 + S 4 (400 g + 200 g) | 82% (cv. DEA) |
| 3.5 | H 1 + S 8 (400 g + 200 g) | 76% (cv. DEA) |
| 3.6 | H 1 + S 9 (400 g + 200 g) | 73% (cv. DEA) |
| 3.7 | H 1 + S 10 (400 g + 200 g) | 79% (cv. DEA) |
| 3.8 | H 1 + S 10 (300 g + 300 g) | 68% (cv. Lorenzo) |
| 3.9 | H 1 + S 11 (300 g + 300 g) | 84% (cv. Lorenzo) |
| 3.10 | H 1 + S 12 (300 g + 300 g) | 56% (cv. Lorenzo) |
| 3.11 | H 1 + S 13 (300 g + 300 g) | 37% (cv. Lorenzo) |
| 3.12 | H 1 + S 14 (300 g + 300 g) | 37% (cv. Lorenzo) |
| 3.13 | H 1 + S 15 (100 g + 100 g) | 53% (cv. Lorenzo) |
| 3.14 | H 1 + S 16 (100 g + 100 g) | 77% (cv. Lorenzo) |
| 3.15 | H 1 + S 17 (80 g + 80 g) | 58% (cv. Lorenzo) |

TABLE 4 postemergence, greenhouse

| No. | Herbicide + safener | Combination according to the invention Reduction of the phytotoxicity in corn by x percent |
|---|---|---|
| 4.1 | H 1 + S 1 (200 g + 100 g) | 50% (cv. DEA) |
| 4.2 | H 1 + S 4 (200 g + 100 g) | 50% (cv. DEA) |
| 4.3 | H 1 + S 5 (200 g + 100 g) | 50% (cv. DEA) |
| 4.4 | H 1 + S 6 (200 g + 100 g) | 57% (cv. DEA) |
| 4.5 | H 1 + S 7 (200 g + 100 g) | 50% (cv. DEA) |
| 4.6 | H 1 + S 8 (200 g + 100 g) | 67% (cv. DEA) |
| 4.7 | H 1 + S 10 (200 g + 100 g) | 72% (cv. DEA) |

TABLE 5 preemergence (herbicide 1, safener 8), outdoors

| No. | Application rate herbicide [g of ai/ha] + safener [g of ai/ha] | Reduction of the phytotoxicity in corn by x percent |
|---|---|---|
| 5.1 | 75 + 75 | 100% |
| 5.2 | 150 + 150 | 64% |
| 5.3 | 300 + 300 | 65% |

TABLE 6 seed dressing, preemergence (herbicide 1, safener 8), outdoors

| No. | Application rate herbicide [g of ai/ha] + safener [g/kg of seed] | Reduction of the phytotoxicity in corn by x percent |
|---|---|---|
| 6.1 | 200 + 1 | 100% |
| 6.2 | 200 + 4 | 100% |

TABLE 7 seed dressing, preemergence (herbicide 1, safener 10), outdoors

| No. | Application rate herbicide [g of ai/ha] + safener [g/kg of seed] | Reduction of the phytotoxicity in corn by x percent |
|---|---|---|
| 7.1 | 200 + 0.5 | 100% |
| 7.2 | 200 + 1 | 100% |

We claim:
1. A herbicidally active composition, comprising a mixture of
   A) a herbicidally effective amount of one or more compounds of the formula (I)

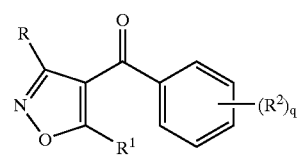

(I)

where the symbols and indices are as defined below:
R is hydrogen or $(C_1-C_4)$-alkoxycarbonyl;
$R^1$ is hydrogen, $(C_1-C_4)$-alkyl, $(C_2-C_4)$-alkenyl, $(C_2-C_4)$-alkynyl, $(C_3-C_8)$-cycloalkyl, $(C_3-C_8)$-cycloalkenyl, $(C_1-C_4)$-alkyl-$(C_3-C_8)$-cycloalkyl, $(C_3-C_7)$-halocycloalkyl, $(C_1-C_4)$-alkylthio-$(C_3-C_8)$-cycloalkyl, $(C_1-C_8)$-haloalkyl or $(C_2-C_8)$-haloalkenyl, preferably $(C_3-C_7)$-cycloalkyl, $(C_1-C_4)$-alkyl-$(C_3-C_7)$-cycloalkyl;
$R^2$ are identical or different radicals from the group consisting of halogen, nitro, cyano, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_2-C_4)$-haloalkynyl, $(C_1-C_4)$-alkoxy-$(C_1-C_4)$-alkyl, $(C_1-C_4)$-alkylthio, $(C_1-C_4)$-alkylsulfinyl, $(C_1-C_4)$-alkylsulfonyl, $(C_1-C_4)$-alkoxy-$(C_1-C_4)$-alkoxy, $(C_1-C_4)$-alkylcarbonyl, $(C_1-C_4)$-alkylsulfonylamino, $(C_1-C_4)$-alkoxy, $(C_1-C_4)$- alkoxycarbonyl, $(C_1-C_4)$-alkylaminosulfonyl, $(C_1-C_4)$-dialkylaminosulfonyl, $(C_1-C_4)$-dialkylcarbamoyl, $(C_1-C_4)$-haloalkylthio, $(C_1-C_4)$-alkylsulfonyloxy and $(C_1-C_4)$-haloalkoxy;

q is 0, 1, 2, 3 or 4; and

B) an antidotically effective amount of one or more safeners from the group of the acylsulfamoylbenzamides of the formula (II), if appropriate also in the form of a salt,

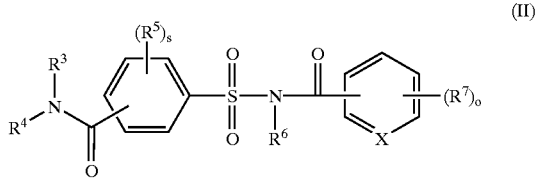

in which

X is CH or N;

$R^3$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl having up to three heteroatoms from the group consisting of nitrogen, oxygen and sulfur, where the seven last mentioned radicals are unsubstituted or substituted by one or more identical or different substituents from the group consisting of halogen, $(C_1-C_6)$-alkoxy, $(C_1-C_6)$-haloalkoxy, $(C_1-C_2)$-alkylsulfinyl, $(C_1-C_2)$-alkylsulfonyl, $(C_3-C_6)$-cycloalkyl, $(C_1-C_4)$-alkoxycarbonyl, $(C_1-C_4)$-alkylcarbonyl and phenyl and, in the case of cyclic radicals, also $(C_1-C_4)$-alkyl and $(C_1-C_4)$-haloalkyl;

$R^4$ is hydrogen, $(C_1-C_6)$-alkyl, $(C_2-C_6)$-alkenyl, $(C_2-C_6)$-alkynyl, where the three last mentioned radicals are unsubstituted or substituted by one or more identical or different substituents from the group consisting of halogen, hydroxyl, $(C_1-C_4)$-alkyl, $(C_1-C_4)$-alkoxy and $(C_1-C_4)$-alkylthio, or $R^3$ and $R^4$ together with the nitrogen atom that carries them form a pyrrolidinyl or piperidinyl radical;

$R^5$ are identical or different radicals from the group consisting of halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulfonyl, $(C_1-C_4)$-alkoxycarbonyl and $(C_1-C_4)$-alkylcarbonyl;

$R^6$ is hydrogen, $(C_1-C_4)$-alkyl, $(C_2-C_4)$-alkenyl or $(C_2-C_4)$-alkynyl;

$R^7$ are identical or different radicals from the group consisting of halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulfinyl, $(C_1-C_4)$-alkylsulfonyl, $(C_1-C_4)$-alkoxycarbonyl or $(C_1-C_4)$-alkylcarbonyl;

s is 0, 1 or 2 and o is 1 or 2, including the stereoisomers and the salts customarily used in agriculture.

2. A herbicidally active composition as claimed in claim 1, where in compounds of the formula (I) the symbols and indices are as defined below:

R is hydrogen or ethoxycarbonyl;

$R^1$ is cyclopropyl and $R^2$ are identical or different radicals from the group consisting of halogen, methyl, ethyl, trifluoromethyl, methylthio, ethylthio, methylsulfonyl, ethylsulfonyl, methoxy, ethoxy, halomethoxy and haloethoxy.

3. A herbicidally active composition as claimed in claim 1, where in compounds of the formula (I) the symbols and indices are as defined below:

$R^2$ are identical or different radicals from the group consisting of chlorine, bromine, fluorine, methyl, ethyl, trifluoromethyl, methylsulfonyl, ethylsulfonyl, methoxy and ethoxy;

q is 2 or 3.

4. A herbicidally active composition as claimed in claim 1, where in compounds of the formula (I) one $R^2$ is a 2-methylsulfonyl radical and a further $R^2$ is a 4-trifluoromethyl, 4-chloro or 4-bromo radical.

5. A herbicidally active composition as claimed in claim 1, where in compounds of the formula (II) the symbols are as defined below:

X is CH;

$R^3$ is hydrogen, $(C_1-C_6)$-alkyl, $(C_3-C_6)$-cycloalkyl, $(C_2-C_6)$-alkenyl, $(C_5-C_6)$-cycloalkenyl or phenyl;

$R^6$ is hydrogen;

$R^7$ are identical or different radicals from the group consisting of halogen, nitro, $(C_1-C_4)$-alkyl, $(C_1-C_4)$-haloalkyl, $(C_1-C_4)$-haloalkoxy, $(C_3-C_6)$-cycloalkyl, $(C_1-C_4)$-alkoxy, cyano, $(C_1-C_4)$-alkylthio, $(C_1-C_4)$-alkylsulfinyl, $(C_1-C_4)$-alkylsulfonyl, $(C_1-C_4)$-alkoxycarbonyl and $(C_1-C_4)$-alkylcarbonyl.

6. A herbicidally active composition as claimed in claim 1, where in compounds of the formula (II) the symbols and indices are as defined below:

$R^3$ is $(C_2-C_6)$-alkynyl or $R^3$ and $R^4$ together with the nitrogen atom that carries them form a pyrrolidinyl or piperidinyl radical and $R^6$ is methyl.

7. A herbicidally active composition as claimed in claim 1, where in the formula (II) the group "$R^3R^4N$—CO—" is located in the 4-position on the phenyl ring.

8. A herbicidally active composition as claimed in claim 1, where the weight ratio herbicide:safener is from 1:100 to 100:1.

9. A herbicidally active composition as claimed in claim 1, additionally comprising a further herbicide.

10. A herbicidally active composition as claimed in claim 9, where the further herbicide is a sulfonylurea.

11. A method for controlling harmful plants in crops of useful plants, which comprises applying a herbicidally effective amount of a herbicidally active composition as claimed in claim 1 to the harmful plants, crop plants, plant seeds or the area in which the plants grow.

12. A method as claimed in claim 11, wherein safener and herbicide are applied at different times.

13. A method as claimed in claim 11, wherein, in a pretreatment step, the seeds are dressed with a safener and, in a further step, the herbicide is applied.

14. A method as claimed in claim 11, wherein the plants are from the group consisting of corn, wheat, rye, barley, oats, rice, sorghum, cotton and soybean.

15. A process as claimed in claim 11, wherein the plants are genetically modified.

* * * * *